United States Patent
Early et al.

(10) Patent No.: US 9,452,056 B2
(45) Date of Patent: Sep. 27, 2016

(54) IMPLANTS FOR FIXATION OF THE DISTAL TIBIA

(71) Applicant: Biomet C.V., Gibraltar (GI)

(72) Inventors: John Early, Dallas, TX (US); Brian Berelsman, Warsaw, IN (US); Paul D'Antonio, Winona Lake, IN (US); Adam Finley, Winona Lake, IN (US)

(73) Assignee: BIOMET C.V., Gibraltar (GI)

( * ) Notice: Subject to any disclaimer, the term of this patent is extended or adjusted under 35 U.S.C. 154(b) by 0 days.

(21) Appl. No.: 14/499,537

(22) Filed: Sep. 29, 2014

(65) Prior Publication Data

US 2016/0089245 A1 Mar. 31, 2016

(51) Int. Cl.
*A61F 2/38* (2006.01)
*A61F 2/42* (2006.01)
*A61F 2/30* (2006.01)

(52) U.S. Cl.
CPC .... *A61F 2/4202* (2013.01); *A61F 2002/30217* (2013.01); *A61F 2002/30235* (2013.01); *A61F 2002/30382* (2013.01); *A61F 2002/4205* (2013.01); *A61F 2002/4207* (2013.01); *A61F 2310/00017* (2013.01); *A61F 2310/00023* (2013.01); *A61F 2310/00029* (2013.01)

(58) Field of Classification Search
CPC ........... A61F 2/28; A61F 2002/30915; A61F 2002/30599
USPC ......... 623/20.32, 20.24, 23.23, 21.18, 23.25, 623/22.41, 22.42
See application file for complete search history.

(56) References Cited

U.S. PATENT DOCUMENTS

| | | | |
|---|---|---|---|
| 4,938,768 A * | 7/1990 | Wu | A61B 17/68 403/307 |
| 5,935,127 A | 8/1999 | Border | |
| 6,120,504 A | 9/2000 | Brumback et al. | |
| 6,264,699 B1 * | 7/2001 | Noiles | A61F 2/30734 623/20.15 |
| 6,319,286 B1 * | 11/2001 | Fernandez | A61F 2/30734 623/16.11 |
| 6,569,203 B1 * | 5/2003 | Keller | A61F 2/389 606/309 |
| 6,613,092 B1 * | 9/2003 | Kana | A61F 2/3859 623/20.15 |
| 6,723,129 B2 * | 4/2004 | Dwyer | A61F 2/30734 623/22.42 |
| 6,843,808 B2 * | 1/2005 | Grundei | A61F 2/2814 623/32 |

(Continued)

OTHER PUBLICATIONS

Horisberger et al., "Commercially Available Trabecular Metal Ankle Interpositional Spacer for Tibiotalocalcaneal Arthrodesis Secondary to Severe Bone Loss of the Ankle," The Journal of Foot & Ankle Surgery 53 (2014) 383-387.

*Primary Examiner* — Alvin Stewart
(74) *Attorney, Agent, or Firm* — Schwegman Lundberg & Woessner, P.A.

(57) ABSTRACT

An ankle implant for implantation at a distal tibia can include a first sleeve augment, a second sleeve augment, an intramedullary (IM) implant and a connecting peg. The first sleeve augment can have a first cannulated sleeve body comprising a first inner solid metal body portion and a first outer porous metal body portion. The IM implant can have an outer augment mounting structure. The second sleeve augment can have a second cannulated sleeve body comprising a second inner solid metal body portion and a second outer porous metal body portion. The second inner solid metal body portion can include a second sleeve first mating structure. The first and second sleeve augments can be assembled onto the IM implant in a stacked orientation with the connecting peg received by both the first sleeve first mating structure and the second sleeve first mating structure in a keyed relationship.

8 Claims, 6 Drawing Sheets

(56) References Cited

U.S. PATENT DOCUMENTS

| | | | |
|---|---|---|---|
| 6,869,450 B2* | 3/2005 | Grundei | A61F 2/2814 623/32 |
| 6,953,479 B2* | 10/2005 | Carson | A61F 2/38 623/20.15 |
| 6,981,991 B2* | 1/2006 | Ferree | A61B 17/164 623/23.15 |
| 7,018,420 B2* | 3/2006 | Grundei | A61F 2/2814 623/32 |
| 7,192,448 B2* | 3/2007 | Ferree | A61B 17/164 623/18.11 |
| 7,323,012 B1 | 1/2008 | Stone et al. | |
| 7,435,263 B2* | 10/2008 | Barnett | A61F 2/28 623/19.12 |
| 7,507,256 B2* | 3/2009 | Heck | A61F 2/28 623/20.15 |
| 7,691,150 B2* | 4/2010 | Cronin | A61F 2/4684 623/20.32 |
| 7,794,503 B2* | 9/2010 | Daniels | A61F 2/36 623/22.11 |
| 7,909,883 B2* | 3/2011 | Sidebotham | A61F 2/2814 623/11.11 |
| 7,993,408 B2 | 8/2011 | Meridew et al. | |
| 8,021,432 B2 | 9/2011 | Meridew et al. | |
| 8,157,869 B2 | 4/2012 | Metzger et al. | |
| 8,292,967 B2 | 10/2012 | Brown et al. | |
| 8,444,699 B2 | 5/2013 | Metzger et al. | |
| 8,535,386 B2* | 9/2013 | Servidio | A61F 2/30734 623/23.28 |
| 8,932,364 B2* | 1/2015 | Mooradian | 623/20.32 |
| 8,998,996 B2* | 4/2015 | James | A61F 2/30734 623/20.14 |
| 2002/0040244 A1* | 4/2002 | Despres, III | A61F 2/30734 623/22.15 |
| 2003/0191531 A1* | 10/2003 | Berry | A61F 2/4455 623/17.11 |
| 2004/0049270 A1* | 3/2004 | Gewirtz | A61F 2/28 623/17.11 |
| 2004/0193267 A1* | 9/2004 | Jones | A61F 2/28 623/16.11 |
| 2005/0004679 A1* | 1/2005 | Sederholm | A61F 2/30734 623/22.42 |
| 2005/0071014 A1* | 3/2005 | Barnett | A61F 2/28 623/19.14 |
| 2005/0107794 A1* | 5/2005 | Hazebrouck | A61F 2/28 606/62 |
| 2006/0036251 A1 | 2/2006 | Reiley | |
| 2006/0036322 A1 | 2/2006 | Reiley | |
| 2006/0229730 A1* | 10/2006 | Railey | A61B 17/15 623/21.18 |
| 2007/0129809 A1* | 6/2007 | Meridew | A61F 2/30724 623/22.32 |
| 2007/0156241 A1 | 7/2007 | Reiley et al. | |
| 2008/0021566 A1* | 1/2008 | Peters | A61F 2/3886 623/20.16 |
| 2008/0065212 A1 | 3/2008 | Zucherman et al. | |
| 2008/0154316 A1 | 6/2008 | Reiley | |
| 2008/0281430 A1* | 11/2008 | Kelman | A61F 2/30734 623/23.23 |
| 2008/0306603 A1* | 12/2008 | Reich | A61F 2/389 623/20.15 |
| 2009/0011384 A1* | 1/2009 | Collins | A61C 8/0012 433/174 |
| 2009/0259261 A1 | 10/2009 | Reiley | |
| 2010/0003640 A1* | 1/2010 | Damstra | A61C 8/0012 433/201.1 |
| 2010/0179658 A1* | 7/2010 | Freeman | A61F 2/44 623/17.12 |
| 2010/0292738 A1 | 11/2010 | Reiley | |
| 2010/0298947 A1* | 11/2010 | Unger | A61F 2/38 623/20.32 |
| 2011/0087294 A1* | 4/2011 | Reiley | A61B 17/1615 606/279 |
| 2011/0087296 A1 | 4/2011 | Reiley et al. | |
| 2011/0118796 A1 | 5/2011 | Reiley et al. | |
| 2011/0178604 A1* | 7/2011 | Porter | A61F 2/30 623/19.14 |
| 2011/0202141 A1* | 8/2011 | Metzger | A61F 2/28 623/23.14 |
| 2011/0208189 A1* | 8/2011 | Faccioli | A61B 17/72 606/62 |
| 2011/0208315 A1* | 8/2011 | Anapliotis | A61F 2/38 623/20.24 |
| 2012/0197255 A1 | 8/2012 | Elghazaly | |
| 2013/0204387 A1* | 8/2013 | Meridew | A61F 2/30749 623/22.32 |
| 2014/0277532 A1* | 9/2014 | Teeny | A61F 2/38 623/20.24 |
| 2014/0277538 A1* | 9/2014 | Sander | A61F 2/30734 623/20.32 |
| 2015/0134071 A1* | 5/2015 | Luna | A61B 17/15 623/21.18 |
| 2015/0173904 A1* | 6/2015 | Stark | A61F 2/4644 623/18.11 |

* cited by examiner

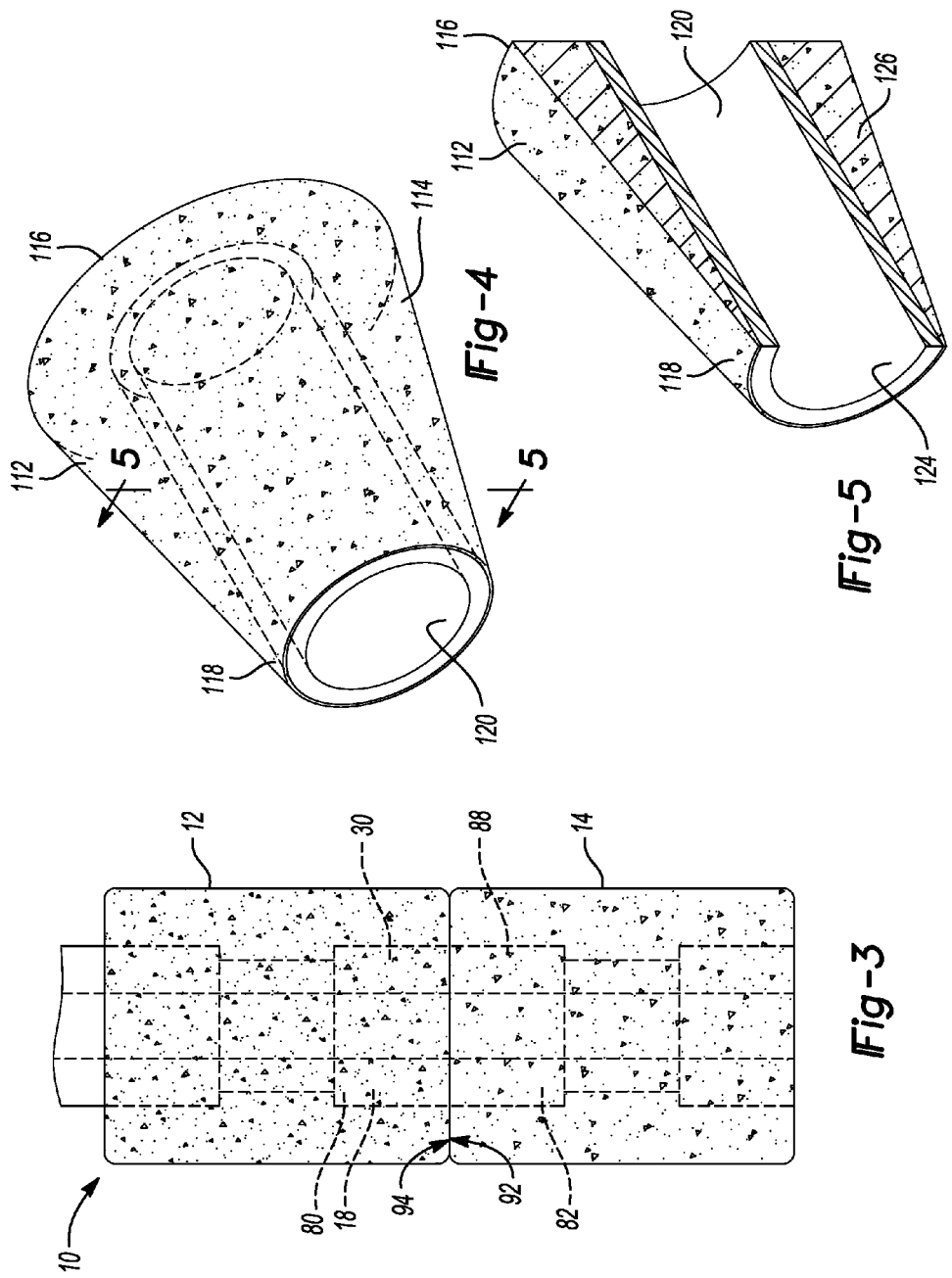

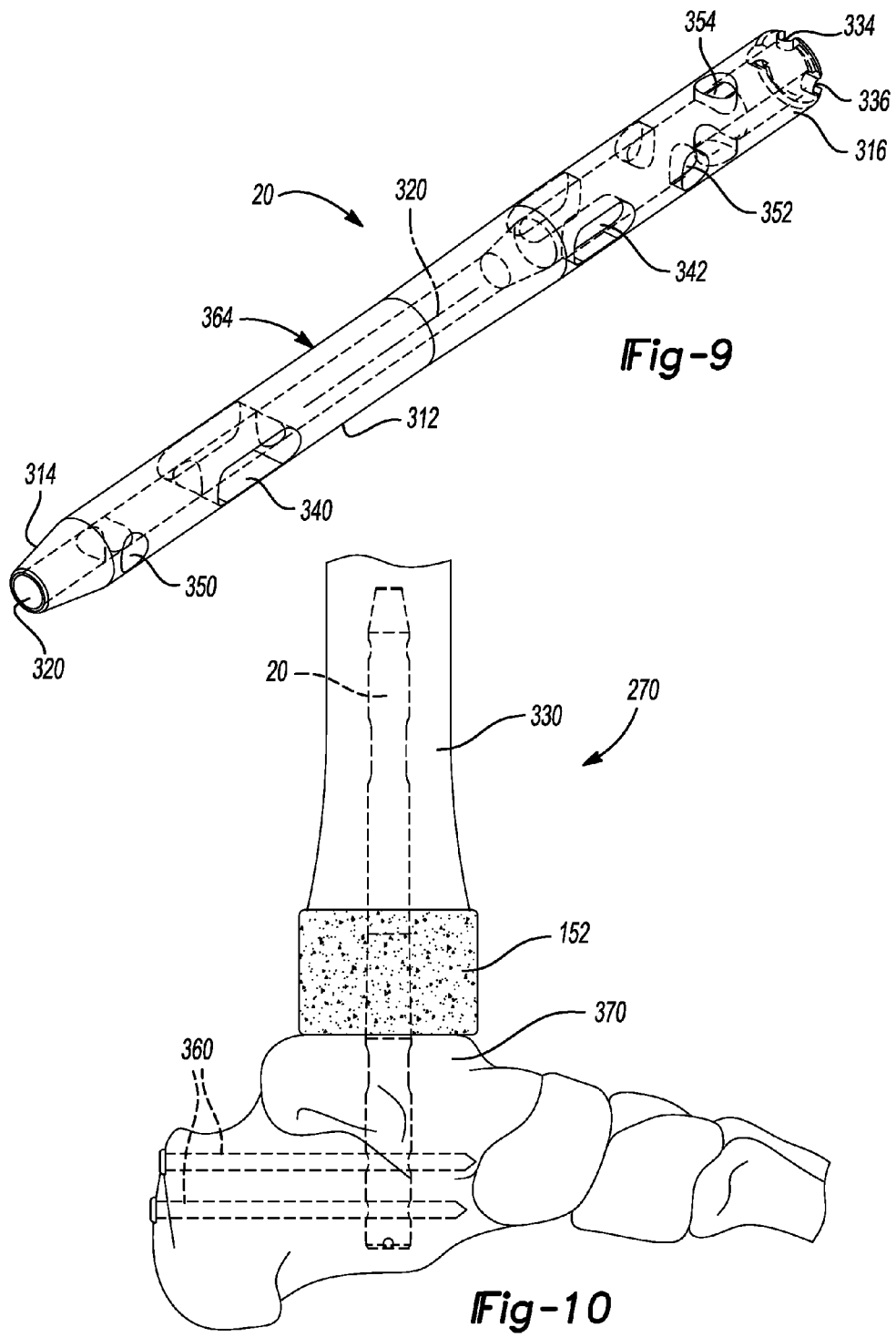

IMPLANTS FOR FIXATION OF THE DISTAL TIBIA

FIELD

The present disclosure relates generally to an implant configuration for stabilizing a fracture and more particularly to an implant and augment configuration for stabilizing a fracture of the distal tibia.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Surgical or medical procedures are often performed on a body, for example, a human body or anatomy, to repair or replace various portions thereof. For example, after trauma, there may be a need to fix bone fragments together to immobilize the fragments and permit healing. One area of the body that presents challenges is the ankle. Various known procedures for the ankle include total ankle arthroplasty (TAA) and ankle fusion. Such procedures can involve implanting various implants including plates and nails to facilitate healing of a distal tibia fracture. In some instances, however, further distal tibial fractures, general loss of bone and/or poor bone quality due to osteoporosis can lead to subsidence of these implants.

SUMMARY

This section provides a general summary of the disclosure, and is not a comprehensive disclosure of its full scope or all of its features.

An ankle implant for implantation at a distal tibia can include a first sleeve augment, a second sleeve augment, an intramedullary (IM) implant and a connecting peg. The first sleeve augment can have a first cannulated sleeve body comprising a first inner solid metal body portion and a first outer porous metal body portion. The first inner solid metal body portion can include a first sleeve first mating structure. The IM implant can have a longitudinal body that extends from a first end to a second end along a longitudinal axis. The IM implant can have an outer augment mounting structure. The second sleeve augment can have a second cannulated sleeve body comprising a second inner solid metal body portion and a second outer porous metal body portion. The second inner solid metal body portion can include a second sleeve first mating structure. The connecting peg can define a cannulation and includes an outer peg mounting feature. The first and second sleeve augments can be assembled onto the IM implant in a stacked orientation with the connecting peg received by both the first sleeve first mating structure and the second sleeve first mating structure in a keyed relationship.

According to additional features, the first sleeve first mating structure can include a first pair of opposing sidewalls. The first sleeve first mating structure can further include a second pair of opposing sidewalls. The first and second pairs of opposing sidewalls can generally be transverse relative to each other. The outer peg mounting feature can comprise an outer peg surface having a geometry complementary for receipt between the first pair of opposing sidewalls. Opposing end surfaces of the first and second sleeve augments can engage each other in the stacked orientation. The first sleeve augment can comprise a shelf surface configured to engage a terminal end surface of the peg. The first sleeve augment can have a central cannulation surface configured to align with the peg cannulation. The connecting peg can be formed of solid biocompatible metal. The porous metal body portion can be formed of at least one of stainless steel, titanium, titanium alloys, polyether ether ketone (PEEK) and cobalt-chromium alloys.

An ankle implant for implantation at a distal tibia constructed in accordance to additional features of the present disclosure can include a sleeve augment and an intramedullary (IM) implant. The sleeve augment can have a cannulated sleeve body comprising (i) an inner solid metal body portion, (ii) an intermediate porous metal body portion, and (iii) an outer solid metal body portion. The inner solid metal body portion can include a sleeve mounting structure. The IM implant can have a longitudinal body that extends from a first end to a second end along a longitudinal axis. The IM implant can have an outer augment mounting structure configured to receive and engage the sleeve mounting structure. The sleeve augment can be assembled onto the IM implant at a location to encourage boney ingrowth of the distal tibia into the intermediate porous metal body portion.

According to additional features, the sleeve augment is cylindrical. In other examples, the sleeve augment is conical. In one conical configuration, an inner portion can be formed of solid material and an outer portion can be formed of porous material. The sleeve augment can extend between terminal ends. The intermediate porous metal body portion can extend entirely between the terminal ends. The sleeve augment can be assembled onto the IM implant at a location to encourage boney ingrowth of a talus. The porous metal body portion can be formed of at least one of stainless steel, titanium, titanium alloys and cobalt-chromium alloys.

A method for stabilizing a fracture of a distal tibia according to one example of the present disclosure is provided. The distal tibia can be initially assessed. A size of an augment can be determined based on the assessment. An augment assembly can be selected based on the determining. The augment assembly can have a solid metal portion and a porous metal portion. The augment assembly can be coupled together. A connecting member can be advanced into a first and second sleeve augment. The augment assembly can be placed at the distal tibia. The augment assembly can be fixed at the distal tibia. The porous metal portion can be configured to facilitate boney ingrowth of the distal tibia.

According to other features of the instant method, an intramedullary (IM) implant can be advanced into an intramedullary canal of the tibia. The IM implant can be passed through cannulations defined by the first sleeve augment, the connecting member and the second sleeve augment. Connecting screws can be advanced into bores defined by the IM implant.

Further areas of applicability of the present disclosure will become apparent from the description provided hereinafter. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only and are not intended to limit the scope of the present disclosure.

FIG. 3 is a front view of a pair of stacking sleeve augments stacked onto each other using a connecting peg according to various aspects of the present disclosure;

FIG. 4 is a perspective view of an exemplary cone sleeve augment in accordance with various aspects of the present disclosure;

FIG. 5 is a sectional view of the stacking sleeve augment of FIG. 4 according to various aspects of the present disclosure;

FIG. 9 is a perspective view of an intramedullary implant according to various aspects of the present disclosure;

FIG. 10 is a lateral view of an ankle having a bone replacement augment and intramedullary nail implanted according to various aspects of the present disclosure;

DETAILED DESCRIPTION

The following description is merely exemplary in nature and is not intended to limit the present disclosure, its application, or uses. Although the following description is related generally to methods and apparatus for bone fracture fixation in a tibia, it should be appreciated that the methods and apparatus discussed herein can be applicable to various other bones and/or joints of the anatomy and can be utilized with various other fixation systems and/or devices.

Exemplary embodiments are provided so that this disclosure will be thorough, and will fully convey the scope to those who are skilled in the art. Numerous specific details are set forth such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Figure 1:
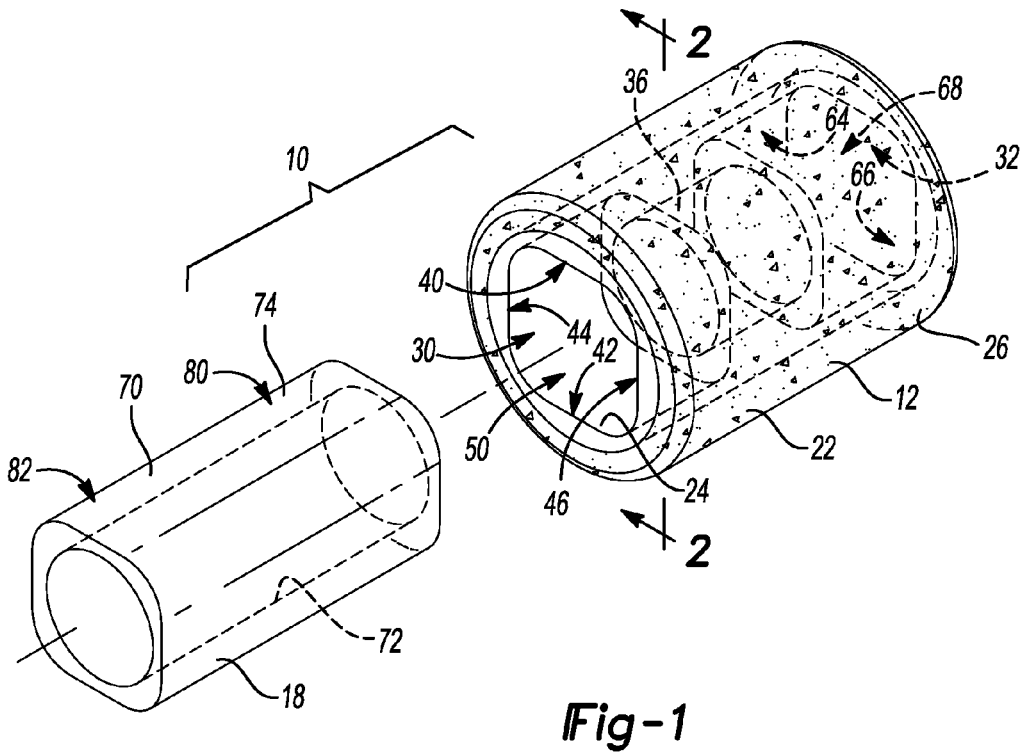
FIG. 1 is a perspective view of an exemplary stacking sleeve augment and connecting pin in accordance with various aspects of the present disclosure.
Figure 2:
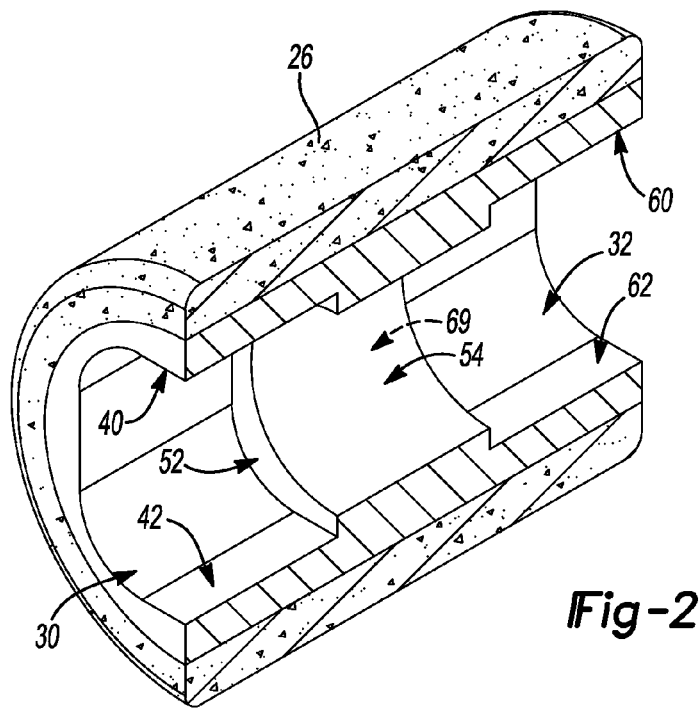
FIG. 2 is a sectional view of the stacking sleeve augment of FIG. 1 according to various aspects of the present disclosure.

With initial reference to FIGS. 1-3, an augment assembly constructed in accordance to one example of the present disclosure is shown and generally identified at reference numeral 10 (FIG. 3). As will become appreciated from the following discussion, the present disclosure provides various augments that offer fixation and/or stabilization methods for total ankle arthroplasty (TAA) and/or revision TAA, ankle fusion and/or Pilon fractures. Additionally, the various augments disclosed herein can incorporate portions of solid metal and porous metal. The porous metal can be used in locations desirable for boney ingrowth of adjacent bone such as the distal tibia and/or talus.

The augment assembly 10 can generally include a first sleeve augment 12, a second sleeve augment 14 (FIG. 3), and a connecting peg 18. Briefly, the first sleeve augment 12 and the second sleeve augment 14 can be assembled in a stacked relationship using the connecting peg 18 (see FIG. 3). As will become appreciated from the following discussion, a single sleeve augment 12, or multiple sleeve augments may be stacked using one or more connecting pegs 18 to account for the desired amount of bone replacement. Further, the augment assembly 10 can be received around an intramedullary (IM) implant 20 (FIG. 9) in an implanted position (see also FIGS. 10-12).

With specific reference now to FIG. 1, the first sleeve augment 12 can generally include a first cannulated sleeve body 22 comprising a first inner solid metal body portion 24 and a first outer porous metal body portion 26. The first inner solid metal body portion 24 can include a first sleeve first mating structure 30. The first sleeve augment 12 can also include a first sleeve second mating structure 32. The sleeve body 22 can define a sleeve cannulation 36. The inner solid metal body portion 24 can be formed of a solid biocompatible metal such as stainless steel, titanium, titanium alloy and cobalt-chromium alloy. Similarly, the outer porous metal body portion 26 can be formed of at least one of stainless steel, titanium, titanium alloy, tantalum, polyether ether ketone (PEEK) and cobalt-chromium alloy. One suitable porous metal includes OsseoTi porous metal marketed by Biomet Manufacturing LLC, of Warsaw, Ind. According to various examples, the solid metal body portion 24 and/or porous metal body portion 26 may include biologics such as demineralized bone matrix (DBM), bone morphogenetic proteins (BMP) and antibiotics. According to other features, the porous metal body portion 26 may include at least one of an anti-infective agent, osteoconductive agent, autologous blood product, hydrogels, autologous cells, allogenic cells, peptides, and bulk allograft. The second sleeve augment 14 can be constructed similarly to the first sleeve augment 12.

The first sleeve first mating structure 30 can include a first pair of opposing sidewalls 40, 42 and a second pair of opposing sidewalls 44, 46. In the example shown, the first and second pairs of opposing sidewalls 40, 42 and 44, 46 are generally transverse relative to each other. The first and second pairs of opposing sidewalls 40, 42 and 44, 46 cooperate to define a keyed female receiving portion 50. The keyed female receiving portion 50 can be further defined by a shelf surface 52 (FIG. 2). The shelf surface 52 can engage a terminal end of the connecting peg 18 when assembled. A central cannulation surface 54 can be generally formed by the inner solid metal body portion 24 that axially separates the first sleeve first mating structure 30 from the first sleeve second mating structure 32.

The first sleeve second mating structure 32 can generally include a first pair of opposing sidewalls 60, 62 and a second pair of opposing sidewalls 64, 66. The first and second pairs of opposing sidewalls 60, 62 and 64, 66 can be generally transverse relative to each other. The first and second pairs of opposing sidewalls 60, 62 and 64, 66 cooperate to define a keyed female receiving portion 68. The keyed female receiving portion 68 can further be defined by a shelf surface 69. The shelf surface 69 can engage a terminal end of another connecting peg 18.

The connecting peg 18 can generally include a peg body 70 that defines a peg cannulation 72 therethrough and has an outer peg mating structure 74. In the example shown, the peg mating structure 74 can include a geometry that is complementary to the keyed female receiving structure 50 of the first sleeve first mating structure 30 (and also the keyed female receiving structure 68 of the first sleeve second mating structure 32). In this regard, the peg body 70 can generally include a first male insertion end 80 and a second male insertion end 82. In the example shown in FIG. 3, the first male insertion end 80 is configured for receipt into the first sleeve first mating structure 30.

The second male insertion end 82 of the connecting peg 18 is shown received by a second sleeve first mating structure 88 provided on the second sleeve 14 (FIG. 3). The configuration of the second sleeve augment 14 is the same as the first sleeve augment 12. In the example shown in FIG. 3, the first sleeve augment 12 includes an end surface 92 that is configured to engage an opposing end surface 94 of the second sleeve augment 14 in an assembled position (FIG. 3). It will be appreciated that while the keyed geometry has been represented as a generally square cross-section, other geometries may be used. In other examples a circular un-keyed geometry may also be used.

Turning now to FIGS. 4 and 5, another sleeve augment constructed in accordance to various examples of the present disclosure is shown and generally identified at reference numeral 112. The sleeve augment 112 can generally include an augment body 114 that extends from a first end 116 to a second end 118. In the example shown, the sleeve body 114 generally tapers from the first end 116 to the second end 118. The sleeve body 114 can further include a cannulation 120 formed therethrough from the first end 116 to the second end 118. The cannulation 120 can be configured to receive the IM implant 20. The augment 114 further includes an inner solid metal body portion 124 and an outer porous metal body portion 126.

Figure 6:
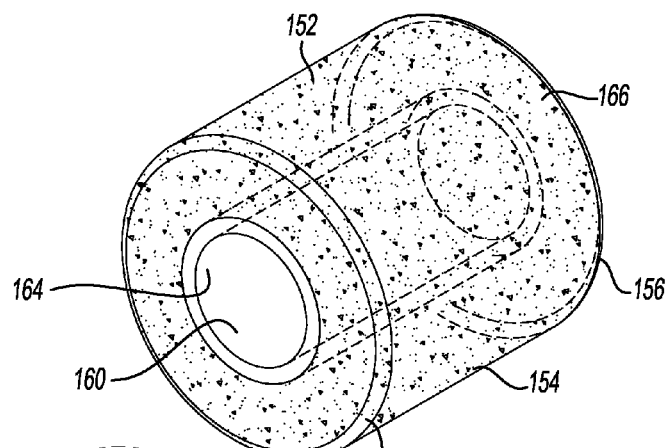
FIG. 6 is a perspective view of a bone replacement augment according to various aspects of the present disclosure.

Turning now to FIG. 6, another sleeve augment constructed in accordance to various features of the present disclosure is shown and generally identified at reference numeral 152. The sleeve augment 152 generally includes an augment body 154 that extends from a first end 156 to a second end 158. The augment body 154 can further define a cannulation 160 that extends from the first end 156 to the second end 158. The cannulation 160 can be configured to receive the IM implant 20. The augment 152 can include an inner solid metal body portion 164 and an outer porous metal body portion 166.

Figure 7:
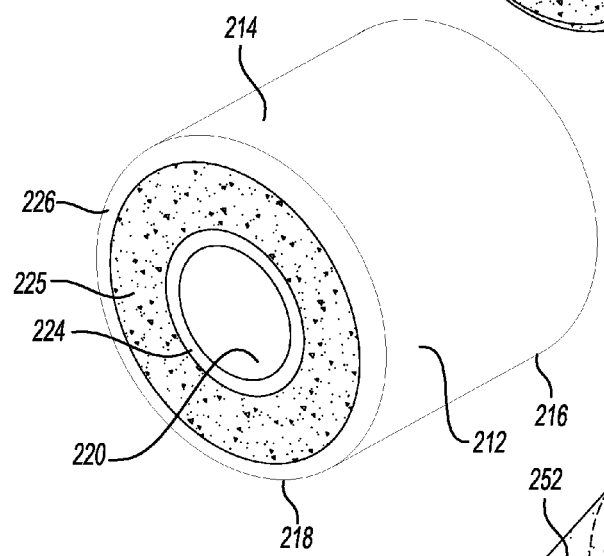
FIG. 7 is a front perspective view of an augment constructed in accordance to another example of the present disclosure.

Turning now to FIG. 7, another sleeve augment constructed in accordance to various features of the present disclosure is shown and generally identified at reference numeral 212. The sleeve augment 212 can generally include an augment body 214 that extends from a first end 216 to a second end 218. The augment body 214 can generally define a cannulation 220 that extends from the first end 216 to the second end 218. The cannulation 220 can be configured to receive the IM implant 20. The sleeve augment 212 can generally include an inner solid metal body portion 224, an intermediate porous metal body portion 225 and an outer solid metal body portion 226. The intermediate porous metal body portion 225 can encourage boney ingrowth of the distal tibia and/or the talus in a longitudinal direction.

Figure 8:
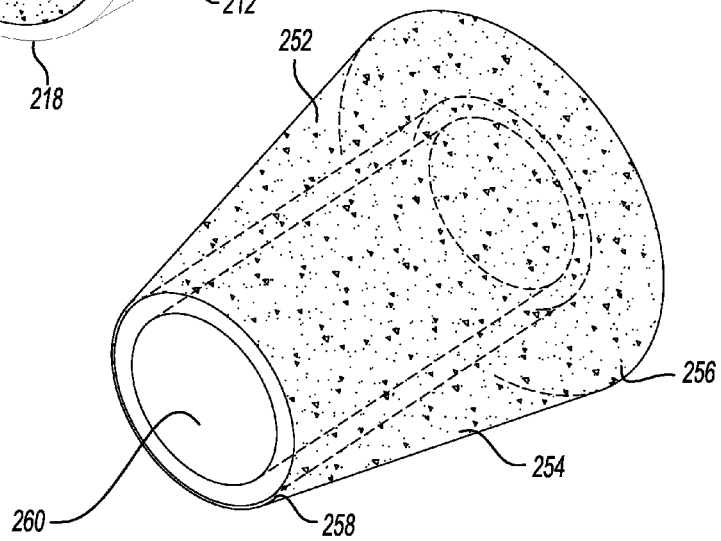
FIG. 8 is a perspective view of a distal cone augment according to various aspects of the present disclosure.

With reference now to FIG. 8, a sleeve augment constructed in accordance to additional features of the present disclosure is shown and generally identified at reference numeral 252. The sleeve augment 252 can generally include an augment body 254 that extends from a first end 256 to a second end 258. In the example shown, the augment body 254 tapers from the first end 256 to the second end 258. The augment 252 can define a central cannulation 260 that extends from the first end 256 to the second end 258. The central cannulation 260 can be configured to receive the IM implant 20. The augment 252 in the example shown is formed entirely of porous metal.

In other examples, any of the augments disclosed herein may have terminal ends that are angled or shaped to match an opposing bone. In this regard, some of the augments may have angled ends configured to oppose and engage jagged or otherwise unsmooth native bone. Moreover, some of the augments may further comprise structural mating features such as a dovetail that is configured to connect with other adjacent distal tibial implants.

Turning now to FIG. 9, an intramedullary (IM) implant constructed in accordance to one example of the present disclosure is shown and generally identified at reference numeral 20. According to various examples of the present disclosure, the IM implant 20 can be used with any of the augments disclosed herein as part of an ankle implant 270. The IM implant 20 can generally include a longitudinal body 312 that extends from a first end 314 to a second end 316 along a longitudinal axis 320. A hollow guide bore 322 can extend between the first end 314 and the second end 316 so that the IM implant can be positioned in a tibia 330 with the aid of a conventional guide pin. In the example provided, notches 334 and 336 can be formed in the second end 316. A first lateral slot 340 can be formed in the IM implant 20, a second lateral slot 342 can similarly be formed in the IM implant 20. Various bores 350, 352, 354 can be formed through the IM implant 20 for receipt of connecting screws such as the connecting screws 360 shown in FIG. 10. The longitudinal body 312 can further include an outer augment mounting surface 364 that is configured to receive and engage the various cannulated portions of the augments disclosed herein.

Figure 11:
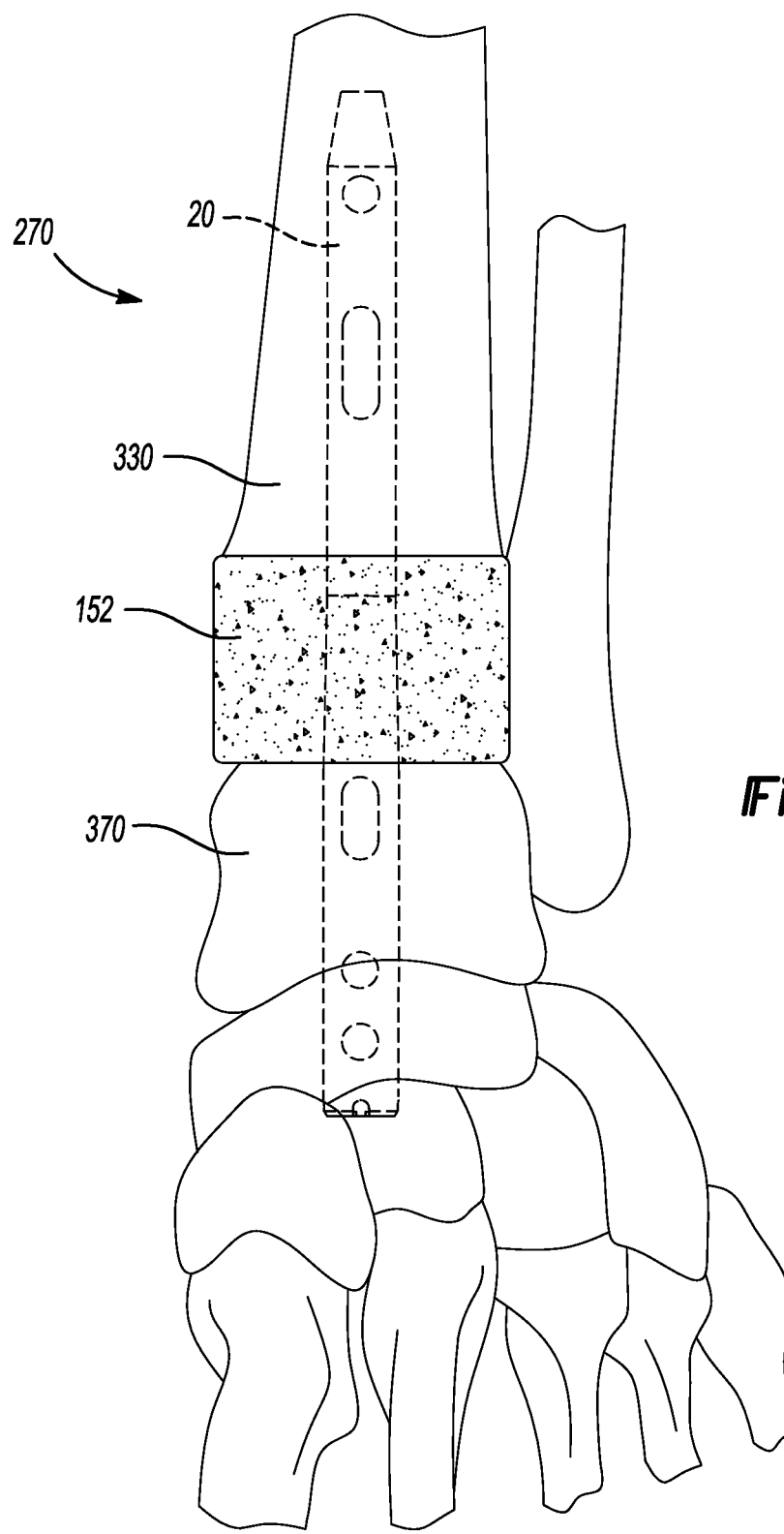
FIG. 11 is an anterior view of an ankle having an ankle implant including a bone replacement augment and intramedullary nail implanted according to various aspects of the present disclosure.
Figure 12:
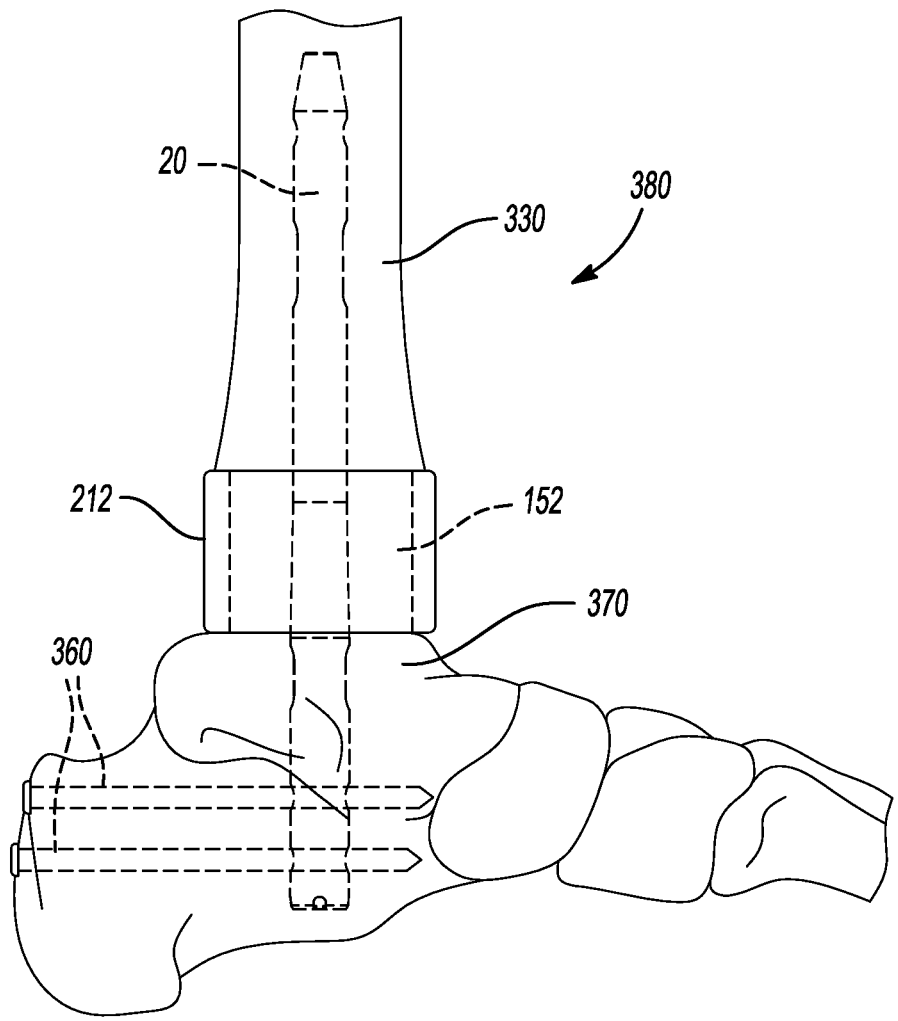
FIG. 12 is a lateral view of an ankle having an ankle implant including the augment of FIG. 7 and intramedullary nail shown in accordance to one example of the present disclosure.

With reference now to FIGS. 10 and 11, the ankle implant 270 is shown as comprising the IM implant 20 and the sleeve augment 152. In the example shown, portions of the distal tibia 330 have been removed for accommodating the sleeve augment 152. It will be appreciated that any of the augments disclosed herein may be implanted generally in the location shown for augment 152 in FIGS. 10 and 11 according to the needs of a particular patient. As shown in FIGS. 10 and 11, the sleeve augment 152 is positioned in a location for engagement between the distal tibia 330 and a talus 370. In this regard, the porous metal portions of the sleeve augment 152 are configured to receive boney ingrowth from the tibia 330 and the talus 370.

The augments disclosed herein can be used in conjunction with other total ankle arthroplasty implants or fusion implants to help augment the arthritic, fractured or osteopenic bone. The augments would help the initial and long term survival of the implants making it easier for a surgeon to create a more stable construct when faced with distal tibia bone issues. Additionally, Pilon fractures could also be treated with these augments.

An exemplary method of stabilizing a fracture of the distal tibia 330 will now be described. Initially, the distal tibia is assessed to determine bone loss, and/or poor bone quality such as due to osteoporosis. Based on the assessment an augment or augment assembly is selected. For example, a surgeon may select a first sleeve augment 12, a second sleeve augment 14 and a connecting member 18 to couple the first and second sleeve augments 12, 14 together. The selection of augments can also consider the porous metal configuration of augment. In this regard, it may be desirable to use an augment having porous metal on the outer surfaces (such as the augments 12, 14, 112, 152 and 252). In other examples it may be desirable to use an augment having solid metal on an outer surface and porous metal on an intermediate surface (such as the augment 212). Once the augment or augment assembly is selected, it is placed at the desired location relative to the distal tibia 330. An intramedullary implant 20 can then be advanced to a location as shown in FIG. 10. During the advancing, the intramedullary implant 20 is passed through the respective cannulations. The augment assembly can then be further fixed by advancing the connecting screws 360 into bores defined in the intramedullary implant 20.

The terminology used herein is for the purpose of describing particular example implementations only and is not intended to be limiting. As used herein, the singular forms "a," "an," and "the" may be intended to include the plural forms as well, unless the context clearly indicates otherwise. The term "and/or" includes any and all combinations of one or more of the associated listed items. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. An ankle implant for implantation at a distal tibia, the ankle implant comprising:
    a first sleeve augment having a first cannulated sleeve body comprising a first inner solid metal body portion and a first outer porous metal body portion, the first inner solid metal body portion including a first sleeve first mating structure;
    an intramedullary implant having a longitudinal body that extends from a first end to a second end along a longitudinal axis, the intramedullary implant having an outer augment mounting structure;
    wherein the first sleeve augment is assembled onto the intramedullary implant such that the first inner solid metal body portion engages the outer augment mounting structure of the intramedullary implant; and
    a second sleeve augment having a second cannulated sleeve body comprising a second inner solid metal body portion and a second outer porous metal body portion, the second inner solid metal body portion including a second sleeve first mating surface;
    wherein the first and second sleeve augments are assembled onto the intramedullary implant in a stacked orientation with a connecting peg received by both the first sleeve first mating structure and the second sleeve first mating structure in a keyed relationship; and
    wherein opposing end surfaces of the first and second sleeve augments engage each other in the stacked orientation.

2. The ankle implant of claim 1 wherein the first sleeve first mating structure includes a first pair of opposing sidewalls and a second pair of opposing sidewalls.

3. The ankle implant of claim 2 wherein the first and second pairs of opposing sidewalls are generally transverse relative to each other.

4. The ankle implant of claim 2 wherein the outer peg mounting feature comprises an outer peg surface having a geometry complementary for receipt between the first pair of opposing sidewalls.

5. The ankle implant of claim 1 wherein the first sleeve augment comprises a shelf surface configured to engage a terminal end surface of the peg.

6. The ankle implant of claim 5 wherein the first sleeve augment has a central cannulation surface configured to align with the peg cannulation.

7. The ankle implant of claim 1 wherein the connecting peg is formed of solid biocompatible metal.

8. The ankle implant of claim 1 wherein the porous metal body portion is formed of at least one of stainless steel, titanium, titanium alloys, polyether ether ketone (PEEK) and cobalt-chromium alloys.

* * * * *